United States Patent
Ishikawa

(10) Patent No.: US 11,931,008 B2
(45) Date of Patent: Mar. 19, 2024

(54) TREATMENT SUPPORT DEVICE AND METHOD OF SETTING REGION OF INTEREST

(71) Applicant: Shimadzu Corporation, Kyoto (JP)

(72) Inventor: Akihiro Ishikawa, Kyoto (JP)

(73) Assignee: Shimadzu Corporation, Kyoto (JP)

(*) Notice: Subject to any disclaimer, the term of this patent is extended or adjusted under 35 U.S.C. 154(b) by 337 days.

(21) Appl. No.: 17/169,741

(22) Filed: Feb. 8, 2021

(65) Prior Publication Data

US 2021/0378494 A1    Dec. 9, 2021

(30) Foreign Application Priority Data

Jun. 3, 2020  (JP) ................................. 2020-096611

(51) Int. Cl.
|  |  |
|---|---|
| A61B 5/00 | (2006.01) |
| A61B 1/04 | (2006.01) |
| A61B 1/045 | (2006.01) |
| G06T 7/00 | (2017.01) |
| G06T 7/11 | (2017.01) |

(52) U.S. Cl.
CPC .............. *A61B 1/043* (2013.01); *A61B 1/045* (2013.01); *A61B 5/0036* (2018.08); *A61B 5/0037* (2013.01); *A61B 5/0071* (2013.01); *G06T 7/0016* (2013.01); *G06T 7/11* (2017.01); *G06T 2207/10024* (2013.01); *G06T 2207/10064* (2013.01); *G06T 2207/10068* (2013.01)

(58) Field of Classification Search
None
See application file for complete search history.

(56) References Cited

U.S. PATENT DOCUMENTS

2017/0032521 A1*  2/2017  Kubo ................... A61B 5/0071

FOREIGN PATENT DOCUMENTS

WO        2019215905 A1    11/2019

\* cited by examiner

*Primary Examiner* — Carolyn A Pehlke
(74) *Attorney, Agent, or Firm* — Muir Patent Law, PLLC

(57) ABSTRACT

A treatment support device includes an irradiation unit configured to emit treatment light to a medical agent, a fluorescence intensity acquisition unit configured to acquire fluorescence intensity of fluorescence emitted by the fluorescent material of the medical agent excited by the treatment light, and a treatment light imaging unit configured to capture a treatment light image based on the treatment light. The treatment support device is configured such that a first region of interest is capable of being set based on a position of the treatment light in the treatment light image captured by the treatment light imaging unit, the first region of interest being a region for selectively acquiring a temporal change in the fluorescence intensity acquired by the fluorescence intensity acquisition unit.

11 Claims, 8 Drawing Sheets

TREATMENT SUPPORT DEVICE AND METHOD OF SETTING REGION OF INTEREST

CROSS-REFERENCE TO RELATED APPLICATIONS

The priority application number JP2020-096611, entitled "TREATMENT SUPPORT DEVICE AND METHOD OF SETTING REGION OF INTEREST, filed on Jun. 3, 2020, and invented by Akihiro ISHIKAWA upon which this patent application is based is hereby incorporated by reference.

BACKGROUND OF THE INVENTION

Field of the Invention

The present invention relates to a treatment support device and a method of setting a region of interest.

Description of the Background Art

Conventionally, a treatment support device for performing treatment support of cancer treatment by photoimmunotherapy is known. Such a treatment support device is disclosed, for example, in WO 2019/215905.

In photoimmunotherapy, a medical agent containing a fluorescent material causing a photochemical reaction and an antibody that selectively binds to a cancer cell is first administered into a body of a cancer patient. The administered medical agent travels through the body of the cancer patient and binds selectively to an antigen of a cancer cell. Next, light in a specific wavelength range according to the fluorescent material is emitted. With this, the fluorescent material of the medical agent bound to the cancer cell emits fluorescence and causes a photochemical reaction, resulting in a change in the chemical structure of the fluorescent material. This change in the chemical structure of the fluorescent material causes a change in the conformation of the antibody. The conformational change in the antibody bound to the cancer cell damages the membrane of the bound cancer cell to thereby destroy (kill) the cancer cell.

WO 2019/215905 discloses a treatment support device provided with a fluorescence detection unit for detecting fluorescence and a fluorescence image generation unit for generating a fluorescent image based on a signal output by the fluorescence detection unit. The fluorescence detection unit detects fluorescence emitted by the fluorescent material of the medical agent administered into a body of a subject for treatment by photoimmunotherapy. The treatment support device described in WO 2019/215905 is configured to output a fluorescent image generated by the fluorescence image generation unit before treatment and a fluorescence image generated at the time of treatment. In the treatment support device described in WO 2019/215905, a user, such as, e.g., a doctor, confirms the progress of the treatment relative to a cancer cell based on a detected change in the fluorescence by comparing the fluorescent image before the treatment with the fluorescent image at the time of the treatment.

Here, in order to properly grasp the progress of treatment with respect to a cancer cell, it is necessary to selectively acquire the temporal change in the fluorescence intensity in the treatment site where the treatment to the cancer cell is performed.

In the treatment support device described in WO 2019/215905, it is possible to compare the fluorescent image before the treatment with the fluorescent image at the time of the treatment. However, the fluorescence is small in the light intensity, and the fluorescence intensity detected from the treatment site changes depending on conditions, such as, e.g., the irradiation position and the irradiation direction of the light emitted for the treatment. Therefore, in all regions of treatment sites, the fluorescence intensity is not always strong, and therefore the region of the treatment site cannot be easily specified only by the fluorescence intensity of the fluorescent image. For this reason, the region where the progress of the treatment in the treatment site is desired to be grasped cannot always be set with high accuracy. Therefore, within a region in which it is desired to grasp the progress of the treatment in the treatment site, it is desired to accurately set a region (region of interest) for selectively acquiring the temporal change in the fluorescence intensity.

The present invention has been made to solve the above-described problems, and an object of the present invention is to provide a treatment support device and a method of setting a region of interest capable of setting a region for selectively acquiring a temporal change in the fluorescence intensity with high accuracy in a region in which the progress of treatment in a treatment site is desired to be grasped.

SUMMARY OF THE INVENTION

A treatment support device according to a first aspect of the present invention is provided with: an irradiation unit configured to emit treatment light in a specific wavelength range to a medical agent administered to a body of a subject when performing treatment for killing a cancer cell, the medical agent containing a fluorescent material; a fluorescence intensity acquisition unit configured to acquire fluorescence intensity of fluorescence emitted by the fluorescent material of the medical agent excited by the treatment light; and a treatment light imaging unit configured to capture a treatment light image based on the treatment light. The treatment support device is configured such that a first region of interest is capable of being set based on a position of the treatment light in the treatment light image captured by the treatment light imaging unit, the first region of interest being a region for selectively acquiring a temporal change in the fluorescence intensity acquired by the fluorescence intensity acquisition unit.

A method of setting a region of interest according to a second aspect of the present invention includes the steps of: emitting treatment light in a specific wavelength range to a medical agent administered to a body of a subject when performing treatment for killing a cancer cell, the medical agent containing a fluorescent material; acquiring fluorescence intensity of fluorescence emitted by the fluorescent material of the medical agent excited by the treatment light; capturing a treatment light image based on the treatment light; and setting a first region of interest based on a position of the treatment light in the treatment light image captured, the first region of interest being a region for selectively acquiring a temporal change in the fluorescence intensity acquired.

As described above, the treatment support device according to the first aspect of the present invention is provided with a fluorescence intensity acquisition unit for acquiring fluorescence intensity of fluorescence emitted by a fluorescent material of a medical agent excited by treatment light and a treatment light imaging unit for capturing a treatment light image based on the treatment light. And the treatment support device according to the first aspect is configured to be able to set a first region of interest based on the position of the treatment light in the treatment light image captured by the treatment light imaging unit, the first region of interest being a region for selectively acquiring a temporal change in the fluorescence intensity acquired by the fluorescence intensity acquisition unit. With this, based on the position of the treatment light in the treatment light image, the treatment site at which treatment for a cancer cell is performed can be easily specified. As a result, by associating the treatment light image with the position of the fluorescence intensity acquired by the fluorescence intensity acquisition unit, it is possible to provide a treatment support device capable of accuracy setting a first region of interest, which is a region for selectively acquiring a temporal change in fluorescence intensity acquired by the fluorescence intensity acquisition unit, in a region in which the progress of treatment in treatment site is desired to be grasped. Further, the treatment light is excitation light for exciting the fluorescent material of the medical agent and has energy larger than the fluorescence, so that it is easier to detect the treatment light compared with the fluorescence. This also makes it easier to specify the treatment site as compared with the case of specifying the treatment site from the fluorescent image.

In the method of setting the region of interest according to the second aspect of the present invention, as described above, the method includes a step of setting a first region of interest based on a position of the treatment light in the treatment light image captured, the first region of interest being a region for selectively acquiring a temporal change in the fluorescence intensity acquired.

With this, it is possible to easily specify the treatment site at which treatment is performed to a cancer cell based on the position of the treatment light in the treatment light image. As a result, by associating the treatment light image with the position of the acquired fluorescence intensity, it is possible to provide a method of setting a region of interest capable of accurately setting the first region of interest, which is a region for selectively acquiring the temporal change in the acquired fluorescence intensity, in a region in which the progress of the treatment at the treatment site is desired to be grasped. In addition, the treatment light is light for exciting the fluorescent material of the medical agent and has energy larger than the fluorescence, so that it is easier to detect the treatment light compared with the fluorescence. This also makes it easier to specify the treatment site than when specifying the treatment site from the fluorescent image.

DESCRIPTION OF THE PREFERRED EMBODIMENT

Hereinafter, some embodiments in which the present invention is embodied will be described with reference to the attached drawings.

Configuration of Treatment Support Device

Figure 1:
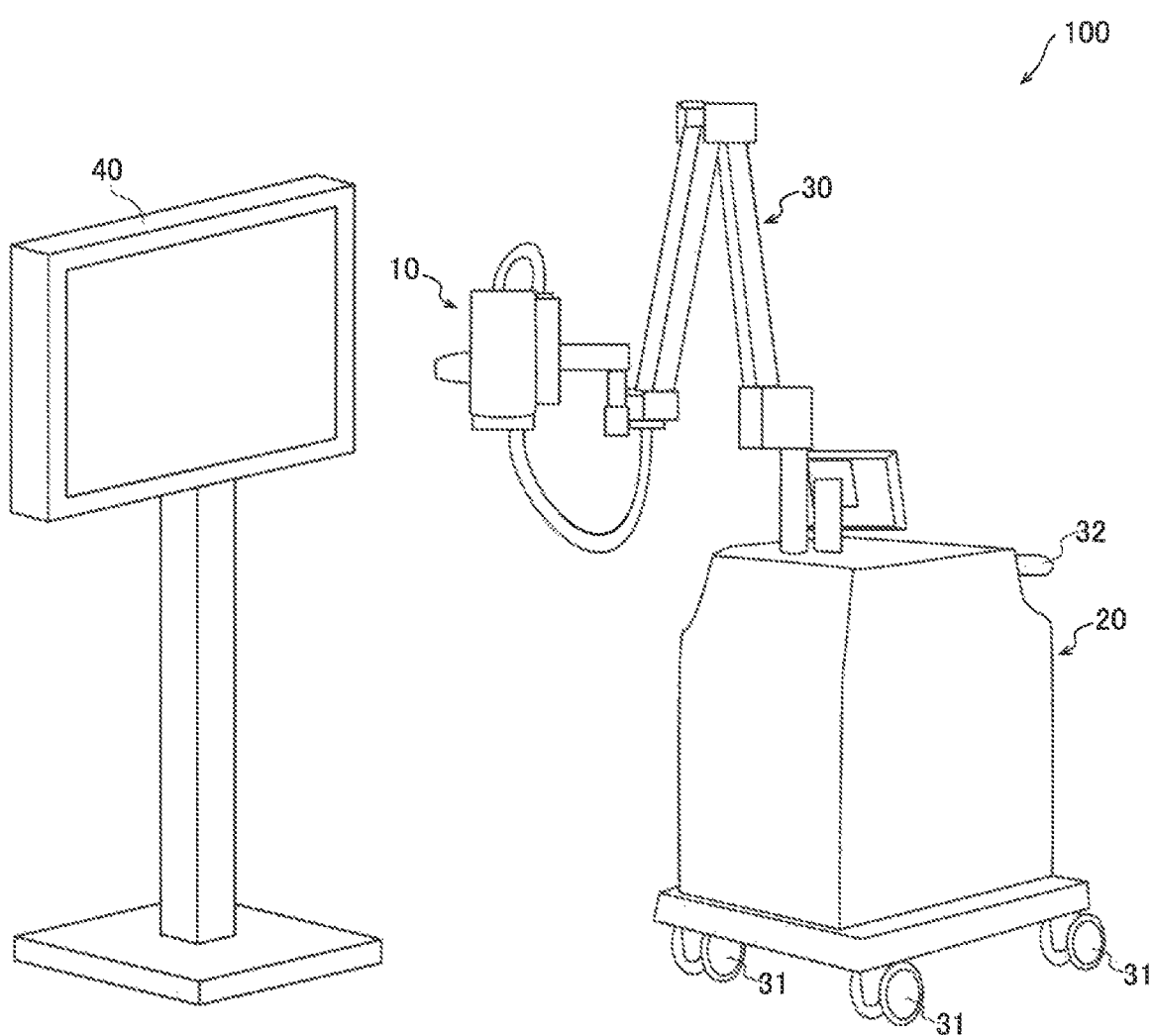
FIG. 1 is a perspective view showing a configuration of a treatment support device according to an embodiment of the present invention.
Figure 2:
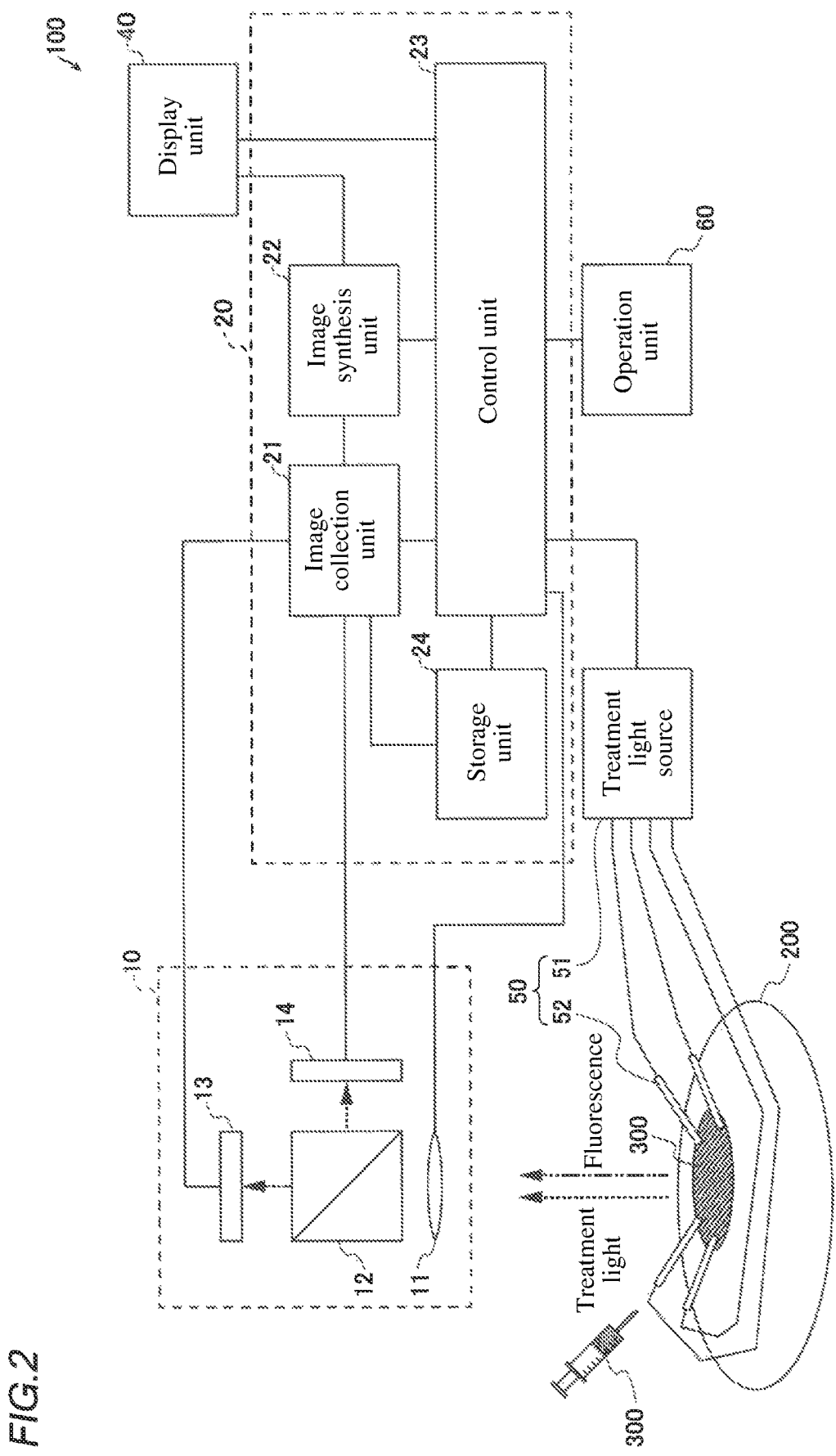
FIG. 2 is a block diagram showing a configuration of a treatment support device according to an embodiment of the present invention.

Referring to FIG. 1 and FIG. 2, a configuration of a treatment support device 100 according to this embodiment will be described.

As shown in FIG. 1, the treatment support device 100 is provided with an imaging unit 10, a device main body 20, and an arm member 30.

The imaging unit 10 is connected to the device main body 20 via the arm member 30. At one end of the arm member 30, the imaging unit 10 is connected, while at the other end of the arm member 30, the device main body 20 is connected. The treatment support device 100 is configured such that the imaging direction and the imaging position of the imaging unit 10 can be adjusted by the arm member 30.

The device main body 20 is provided with, as shown in FIG. 1, a plurality of wheels 31 and a handle portion 32. The device main body 20 is configured as a carriage capable of moving the treatment support device 100 by rotating each of the plurality of wheels 31. The handle portion 32 is configured to be grippable and is provided to be gripped by a user when moving the treatment support device 100.

In this embodiment, the treatment support device 100 is provided with a display unit 40. The display unit 40 is configured by, for example, a liquid crystal display or an organic EL display. The display unit 40 is connected to the control unit 23 (see FIG. 2) by a video interface, such as, e.g., an HDMI (registered trademark) cable.

The treatment support device 100 according to this embodiment is a device for supporting treatment in photoimmunotherapy. Specifically, as shown in FIG. 2, the treatment support device 100 is configured to emit treatment light (excitation light) to a cancer patient 200 to detect the fluorescence emitted by the fluorescent material of the medical agent 300 administered into the body of the cancer patient 200. In addition to the support of the treatment by the photoimmunotherapy, the treatment support device 100 is configured such that treatment by photoimmunotherapy can be performed by continuously emitting treatment light in a specific wavelength range of light according to the fluorescent material of the medical agent 300. Note that the cancer patient 200 is an example of the "subject" in claims.

Further, the treatment support device 100 is provided with an irradiation unit 50 as shown in FIG. 2. The irradiation unit 50 is configured to irradiate the medical agent 300 with the treatment light when performing the treatment of killing a cancer cell based on emitting treatment light in a specific wavelength range to the medical agent 300 containing a fluorescent material administered into the body of the cancer patient 200. That is, the irradiation unit 50 is configured to emit the treatment light (excitation light) to the medical agent 300 containing the fluorescent material administered into the body of the cancer patient 200 when performing the treatment by photoimmunotherapy.

The irradiation unit 50 includes a treatment light source 51 and a plurality of treatment probes 52 (see FIG. 2).

The treatment light source 51 is configured to emit treatment light (excitation light) in a specific wavelength range that excites the fluorescent material contained in the medical agent 300. The treatment light source 51 includes a laser diode (LD: Laser Diode), a light emitting diode (LED: Light Emitting Diode), or the like.

The treatment probe 52 is configured to be inserted into the body of the cancer patient 200 to emit the treatment light within the body of the cancer patient 200.

The treatment probe 52 includes an optical fiber for guiding the light from the treatment light source 51. The treatment probe 52 is inserted along a cylindrical guide (not shown) made of a transparent member such as a glass member, which is to be inserted into the body of the cancer patient 200, toward a position (treatment site) which is a treatment point in the body of the cancer patient 200. A user, such as, e.g., a doctor, grasps the position of the cancer in advance by an MRI (Magnetic Resonance Image), an X-ray CT (Computed Tomography), an ultrasonic wave echo, or the like.

Then, the user, such as, e.g., a doctor, inserts the treatment probe 52 into the body of the cancer patient 200 while confirming the position of the cancer by an ultrasonic wave echo or the like. The treatment probe 52 is inserted at a relatively shallow angle of 20 degrees or less with respect to the cancer patient 200. Specifically, the treatment probe 52 is inserted at a relatively shallow angle of about 10 degrees, or 10 degrees or less, relative to the cancer patient 200. The treatment probe 52 is configured to guide the treatment light from the treatment light source 51 in the body of the cancer patient 200 to illuminate it. Thus, the fluorescent material of the medical agent 300 is excited. The treatment support device 100 can perform the treatment for killing the cancer cell by continuously emitting the treatment light, which is light in a specific wavelength range that excites the fluorescent material contained in the medical agent 300, in the body of the cancer patient 200 by the treatment probe 52.

In photoimmunotherapy, the medical agent 300 (see FIG. 2) is administered into the body of the cancer patient 200 (see FIG. 2) prior to the treatment light irradiation. The medical agent 300 contains a fluorescent material that emits fluorescence and an antibody. The fluorescent material of the medical agent 300 is a substance that is excited to emit fluorescence when irradiated with the treatment light and a substance that causes a photochemical reaction by being continuously irradiated with the treatment light. The fluorescent material is a chemical, such as, e.g., an IRDye (registered mark) 700DX.

In the treatment by photoimmunotherapy, the irradiation unit 50 emits the treatment light corresponding to the type of the fluorescent material of the medical agent 300 administered to the cancer patient 200 to the treatment site (cancer cell) of the cancer patient 200.

Note that the treatment light emitted from the irradiation unit 50 at the time of treatment is light in a wavelength range light in which the fluorescent material of the medical agent 300 used for the treatment causes a photochemical reaction in a wavelength region of 600 nm or more and 2,500 nm or less, which is a region from a part of visible light to near-infrared light, and differs depending on the type of the fluorescent material of the medical agent 300 used for the treatment. For example, when an IRDye (registered mark) 700DX is used for the fluorescent material of the medical agent 300, the irradiation unit 50 emits the light having a peak position of a wavelength of 600 nm or more and 700 nm or less, for example, a non-thermal red light having a peak position of a wavelength of about 690 nm, during the treatment by photoimmunotherapy.

Further, as shown in FIG. 2, the imaging unit 10 of the treatment support device 100 is provided with a lens 11 and a prism 12. As shown in FIG. 2, the imaging unit 10 of the treatment support device 100 is provided with a fluorescence imaging unit 13 and a treatment light imaging unit 14. Note that the fluorescence imaging unit 13 is an example of the "fluorescence intensity acquisition unit" recited in claims.

The lens 11 is configured such that the fluorescence emitted by the fluorescent material of the medical agent 300 and the visible light containing the treatment light emitted by the irradiation unit 50 are incident. The fluorescence and the treatment light including the visible light incident on the lens 11 are converged by the lens 11 and incident on the prism 12.

The prism 12 is configured to separate the incident light. The fluorescence and the visible light including the treatment light incident on the lens 11 are separated by the prism 12. The fluorescence separated by the prism 12 is configured to be imaged at the fluorescence imaging unit 13. The visible light including the treatment light separated by the prism 12 is configured to be imaged at the treatment light imaging unit 14.

The fluorescence imaging unit 13 is configured to acquire the fluorescence intensity emitted by the fluorescent material of the medical agent 300 excited by the treatment light. In this embodiment, the fluorescence imaging unit 13 is configured to acquire (capture) the fluorescent image 41 (see FIG. 3) based on the fluorescence emitted by the fluorescent material of the medical agent 300 excited by the treatment light. The fluorescent image 41 is an image representing the distribution state of the fluorescence emitted by the fluorescent material of the medical agent 300.

The fluorescence imaging unit 13 includes an imaging element for capturing an image based on the fluorescence emitted by the fluorescent material of the medical agent 300 and separated by the prism 12. The imaging element photoelectrically converts the fluorescence into an electric signal. The imaging element is, for example, a CMOS (Complementary Metal Oxide Semiconductor) image sensor, or a CCD (Charge Coupled Device) image sensor.

The fluorescence imaging unit 13 is configured to selectively image the light in a region including the wavelength range of the fluorescence emitted by the fluorescent material of the medical agent 300 by wavelength-selectivity of an optical filter. For example, in a case where an IRDye (registered mark) 700DX is used for the fluorescent material of the medical agent 300, the fluorescence imaging unit 13 is configured to capture the fluorescent image 41 based on the light having a wavelength of 800 nm or more and 860 nm or less by the wavelength selectivity of the optical filter. Note that the IRDye (registered mark) 700DX will be excited by light having a wavelength of 600 nm or more and 700 nm or less to emit light having a peak at a wavelength of about 700 nm or about 770 nm as fluorescence.

Further, the fluorescence imaging unit 13 images the fluorescence emitted by the fluorescent material at a predetermined frame rate such as a frame rate of an NTSC (National Television System Committee) standard.

The treatment light imaging unit 14 is configured to capture the treatment light image 42 (see FIG. 4) based on the treatment light. The treatment light imaging unit 14 includes an imaging element for capturing an image based on the visible light including the treatment light separated by the prism 12. The imaging element photoelectrically converts the visible light including the treatment light into an electric signal. The imaging element is, for example, a CMOS image sensor, a CCD image sensor, or the like.

The treatment light imaging unit 14 is configured to selectively image the light in a region including the wavelength range of the treatment light emitted by the irradiation unit 50 (treatment probe 52) by wavelength-selectivity of an optical filter. In cases where light having a wavelength of 600 nm or more and 700 nm or less, for example, non-thermal red light having a wavelength peak position of about 690 nm, is emitted when performing treatment by photoimmunotherapy, the treatment light imaging unit 14 is configured to perform imaging based on the light having a wavelength of 400 nm or more and 700 nm or less including the wavelength range of the treatment light and the wavelength range of the visible light by wavelength selectivity of an optical filter. That is, the treatment light image 42 includes a visible light image.

Further, the treatment light image 42 is a color image captured based on the light in the wavelength range of the treatment light and the visible light. The treatment light imaging unit 14 images visible light including the treatment light at a predetermined frame rate, such as, e.g., a frame rate of an NTSC standard.

In the device main body 20 of the treatment support device 100, a PC (Personal Computer) including an image collection unit 21, an image synthesis unit 22, a control unit 23, a storage unit 24, and the like, is built-in (see FIG. 2).

The image collection unit 21 is configured so that the image data of the fluorescent image 41 captured by the fluorescence imaging unit 13 and the image data of the treatment light image 42 captured by the treatment light imaging unit 14 are input as electric signals. The image collection unit 21 is configured to collect the data of the fluorescent image 41 and the data of the treatment light image 42 based on the time series.

The treatment support device 100 of this embodiment is configured to be able to acquire the change in the fluorescence intensity in the fluorescent image 41 by the data of the fluorescent image 41 collected along a time series by the image collection unit 21.

Further, the image synthesis unit 22 is configured to generate a synthetic image 43 (see FIG. 7) in which the image data of the fluorescent image 41 and the image data of the treatment light image 42 collected by the image collection unit 21 are superimposed. That is, the image synthesis unit 22 is configured to generate the synthetic image 43 in which a plurality of image data collected by the image collection unit 21 is superimposed.

The image collection unit 21 and the image synthesis unit 22 include a processor, such as, e.g., a GPU (Graphics Processing Unit) and an FPGA (Field-Programmable Gate Array) configured for image processing.

The control unit 23 includes a CPU (Central Processing Unit), a ROM (Read Only Memory), a RAM (Random Access Memory), and the like. The control unit 23 is configured to control the entire treatment support device 100.

The control unit 23 is configured to control the illumination of the treatment light in the body of the cancer patient 200 by the treatment light source 51 via the treatment probe 52. The control unit 23 is configured to control turning on and off the irradiation unit 50 (treatment light source 51). That is, the control unit 23 is configured to control the irradiation and the irradiation stop of the treatment light.

The control unit 23 is configured to analyze the fluorescent image 41 and the treatment light image 42 collected by the image collection unit 21. Further, the control unit 23 is configured to analyze the information of the fluorescence intensity for each time series in the fluorescent image 41. The control unit 23 performs control for selectively acquiring the fluorescence intensity in the treatment site, in the first region of interest (ROI: Region Of Interest) 42c and the second region of interest (ROI) 42d described later.

The storage unit 24 includes, for example, a nonvolatile memory, a hard disk drive (HDD: Hard Disk Drive), an SSD (Solid State Drive), and the like. Further, the storage unit 24 may include a database on a network connected by an external network of the device main body 20.

The storage unit 24 is configured to store image data of the fluorescent image 41 and the treatment light image 42 collected by the image collection unit 21. The storage unit 24 stores, for example, the image data of the fluorescent image 41 and the treatment light image 42 collected by the image collection unit 21 based on the time series together with the time stamp, such as, e.g., the imaging date and time. Further, the storage unit 24 stores a program used for control by the control unit 23. The storage unit 24 is configured to store a program executed by the control unit 23 when image data is collected by the image collection unit 21, a program executed by the control unit 23 to control the irradiation of the treatment light, and data required to control the irradiation of the treatment light.

Further, as shown in FIG. 2, the treatment support device 100 is provided with an operation unit 60. The operation unit 60 is a user interface for operating the treatment support device 100.

The operation unit 60 is configured to receive operations for controlling the illumination of the treatment light by the irradiation unit 50 (treatment light source 51) and the manner of displaying an image displayed on the display unit 40. The operation unit 60 is configured to accept operations for setting the irradiation intensity and the irradiation time of the treatment light emitted by the irradiation unit 50. Further, the operation unit 60 is configured to accept operations for setting the start and end of imaging in the imaging unit 10. Further, the operation unit 60 is configured to accept operations for setting a region of interest, which will be described later. The operation unit 60 includes, for example, a remote controller, a touch panel, a keyboard, a mouse, or the like. Further, a touch panel as the operation unit 60 may be provided on the display unit 40.

Figure 3:
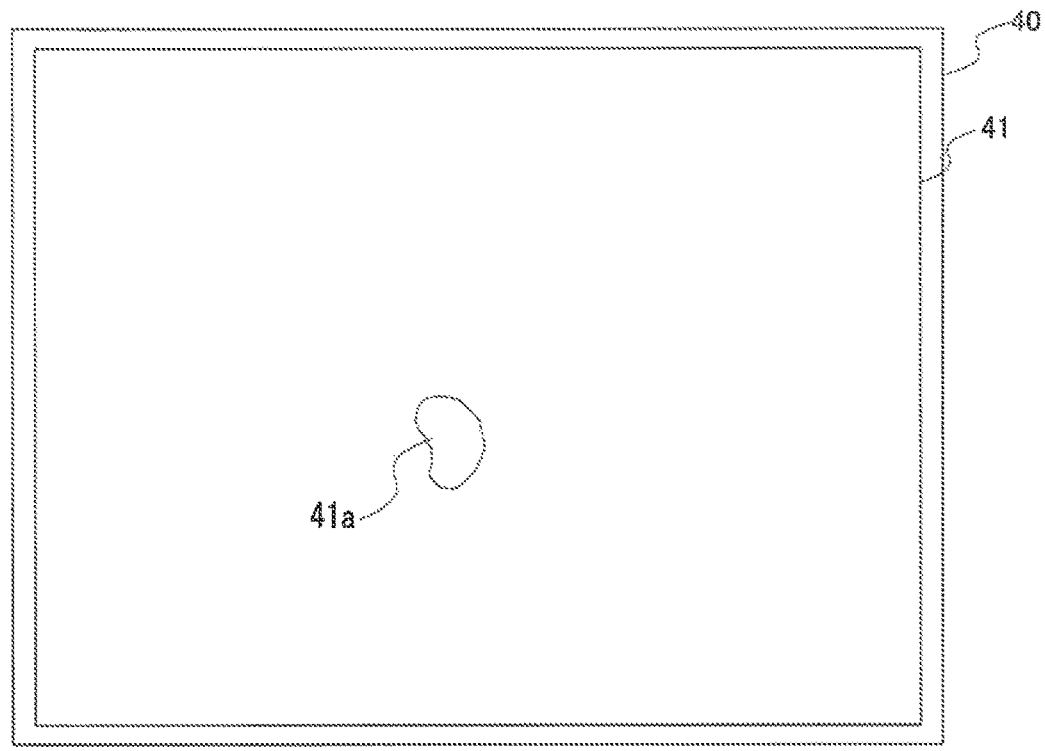
FIG. 3 is a diagram illustrating an example of a fluorescent image displayed on a display unit of a treatment support device.

The display unit 40 is configured to display a fluorescent image 41 as shown in FIG. 3. The fluorescent image 41 is an image showing the distribution status of the fluorescence emitted by the fluorescent material of the medical agent 300. A user, such as, e.g., a doctor, can confirm the accumulation of the medical agent 300 containing the fluorescent material bound to the cancer cell by the distribution 41a of the fluorescence in the fluorescent image 41.

Figure 4:
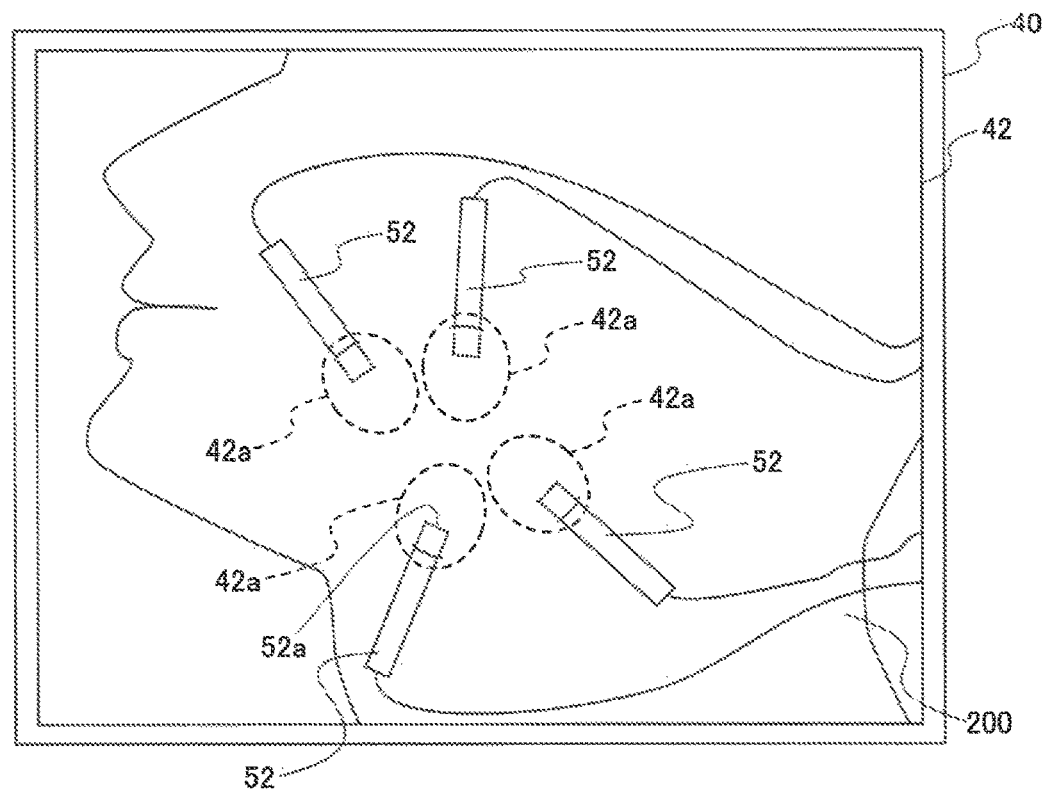
FIG. 4 is a diagram showing an example of a treatment light image displayed on a display unit.

As shown in FIG. 4, the display unit 40 is configured to display a treatment light image 42. In this embodiment, the treatment light image 42 is an image based on the treatment light and the visible light. The image reflects the treatment light leaked out of the body of the cancer patient 200 from the position where the treatment probe 52 is inserted and the treatment light transmitted through the body of the cancer patient 200.

A user, such as, e.g., a doctor, can confirm the positions of the treatment probes 52 inserted into the cancer patient 200 and the treatment light emitted from the treatment probe 52 by the treatment light image 42. As described above, the treatment probe 52 is inserted into the cancer patient 200 to the position of the cancer cell which has been confirmed in advance by a user, such as, e.g., a doctor (see FIG. 4). For this reason, the distal end 52*a* of the treatment probe 52 is inserted so as to face in the direction in which the previously confirmed cancer cell is located. A plurality of treatment probes 52 is inserted so as to surround the position of the cancer, and the treatment to the cancer cell is performed by treatment light emitted from each of them. That is, a region in which the treatment light is emitted from the treatment probe 52 inserted in the body of the cancer patient 200, or a region irradiated with the treatment light and surrounded by a plurality of treatment probes 52 inserted in the body of the cancer patient 200 is the treatment site.

Setting of Region of Interest

The treatment support device 100 is configured such that a first region of interest 42*c* can be set based on the position of the treatment light in the treatment light image 42 captured by the treatment light imaging unit 14. The first region of interest 42*c* is a region for selectively acquiring the change of the fluorescence intensity in the fluorescent image 41. Also, as described above, the fluorescent image 41 is collected based on a time series. In other words, the first region of interest 42*c* is a region for selectively acquiring the temporal change in the fluorescence intensity acquired by the fluorescence imaging unit 13.

In this embodiment, the control unit 23 is configured to perform control for setting the first region of interest 42*c* based on the plurality of treatment light regions 42*a* (see FIG. 4), each of which is a region of the treatment light emitted from each of the plurality of treatment probes 52 in the treatment light image 42 captured by the treatment light imaging unit 14.

Further, in the treatment support device 100 of this embodiment, a user, such as, e.g., a doctor, can visually recognize the treatment light image 42, which is a color image captured based on the light in the wavelength range of the treatment light and the visible light, and can grasp the insertion directions of the treatment probes 52. In the treatment support device 100 of this embodiment, a user, such as, e.g., a doctor, can set the first region of interest 42*c* based on, for example, the position of one or a plurality of treatment probes 52 in the treatment light image 42, the insertion direction of the treatment probe 52, the treatment light, or the treatment light regions 42*a*.

First, as shown in FIG. 4, the control unit 23 is configured to set a plurality of treatment light regions 42*a* in the treatment light image 42, based on the light in the wavelength range of the treatment light. The plurality of treatment light regions 42*a* is a region in which the treatment light emitted from the treatment probe 52 leaked out of the body of the cancer patient 200 from the position where the treatment probe 52 is inserted is imaged, and a region in which the treatment light emitted from the treatment probe 52 and passed through the body of the cancer patient 200 is imaged.

The control unit 23 is configured to set the region of the pixels in the treatment light image 42 in which the brightness of the light in the wavelength range of the treatment light is equal to or higher than a predetermined value as a plurality of treatment light regions 42*a* in the treatment light image 42.

Specifically, a region of pixels in which the gradation of the light in the wavelength range of the treatment light in the treatment light image 42 is equal to or larger than a predetermined value is set as the treatment light region 42*a*. For example, in a case where the wavelength range of the treatment light is about 600 nm to about 800 nm, since the treatment light is in a region of red light to near-infrared light, the region of pixels in which the gradation of R (Red) is equal to or larger than a predetermined value between R (Red), G (Green), and B (Blue) in the treatment light image 42 is defined as the treatment light region 42*a*.

Note that when setting the treatment light region 42*a*, the treatment light region 42*a* may be set based on the gradation value of any one of R, G, and B in the treatment light image 42. Alternatively, the region of pixels whose gradation value of R, G, and B is equal to or greater than the threshold set for R, G, and B, respectively, may be set as the treatment light region 42*a*.

The control unit 23 is configured to set the first region of interest 42*c* based on each of the geometric center positions of the plurality of treatment light regions 42*a* in the treatment light image 42.

Figure 5:
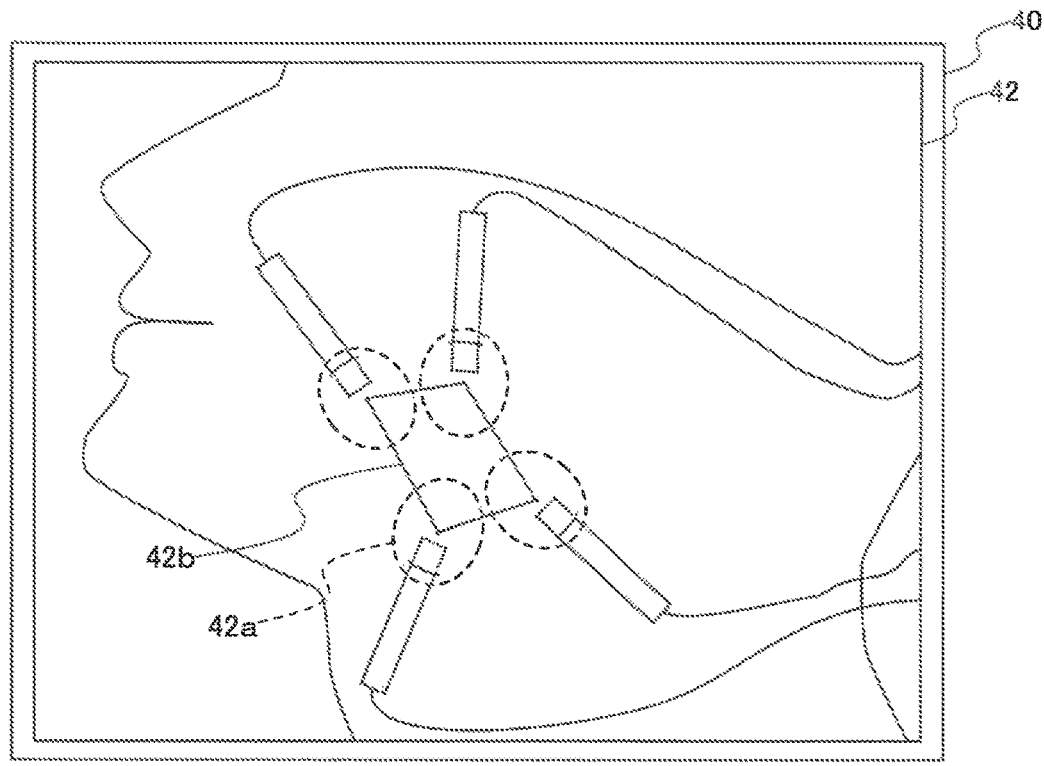
FIG. 5 is a first diagram for explaining setting processing of a first region of interest by a control unit of a treatment support device.

Specifically, the control unit 23 calculates the geometric center position from the area (number of pixels) of each region of the plurality of treatment light regions 42*a* and sets a reference region 42*b* in which the geometric center positions of the plurality of treatment light regions 42*a* are defined as vertices, as shown in FIG. 5.

Figure 6:
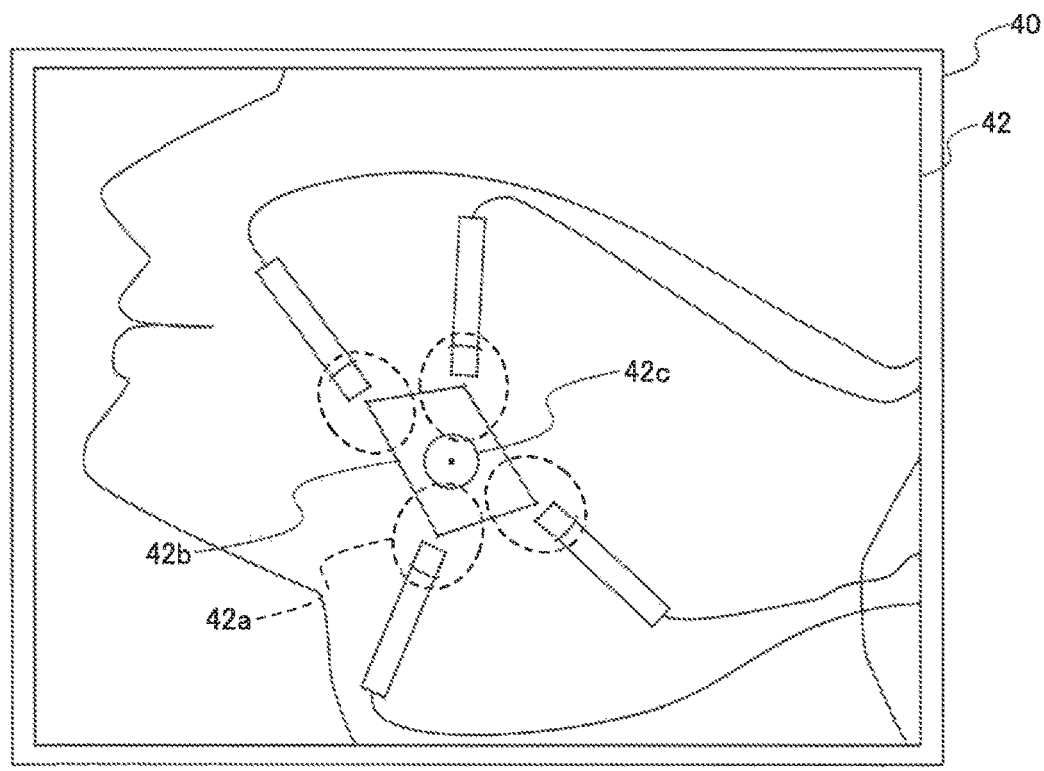
FIG. 6 is a second diagram for explaining setting processing of a first region of interest by a control unit of a treatment support device.

Next, as shown in FIG. 6, the control unit 23 sets the first region of interest 42*c* inside the reference region 42*b*, which is a region surrounded by the geometric center positions of the plurality of treatment light regions 42*a* in the treatment light image 42.

The control unit 23 sets the first region of interest 42*c* so as to be smaller than the reference region 42*b* centering on the geometric center position of the reference region 42*b*.

Specifically, the control unit 23 sets the first region of interest 42*c* centering on the geometric center position of the reference region 42*b*, inside the reference region 42*b*. The first region of interest 42*c* is, as shown in FIG. 6, a circular region centering on the geometric center position of the reference region 42*b*. The circular first region of interest 42*c* is set to be smaller than the reference region 42*b* to be placed inside the reference region 42*b*.

The diameter of the circular first region of interest 42*c* may be a fixed value set in advance, or may be adjustable based on an operation of a user, such as, e.g., a doctor. Further, the region of the set first region of interest 42*c* may be configured to move in accordance with the movement of the periodicity, such as, e.g., the respiration and the pulsation, of the cancer patient 200.

Figure 7:
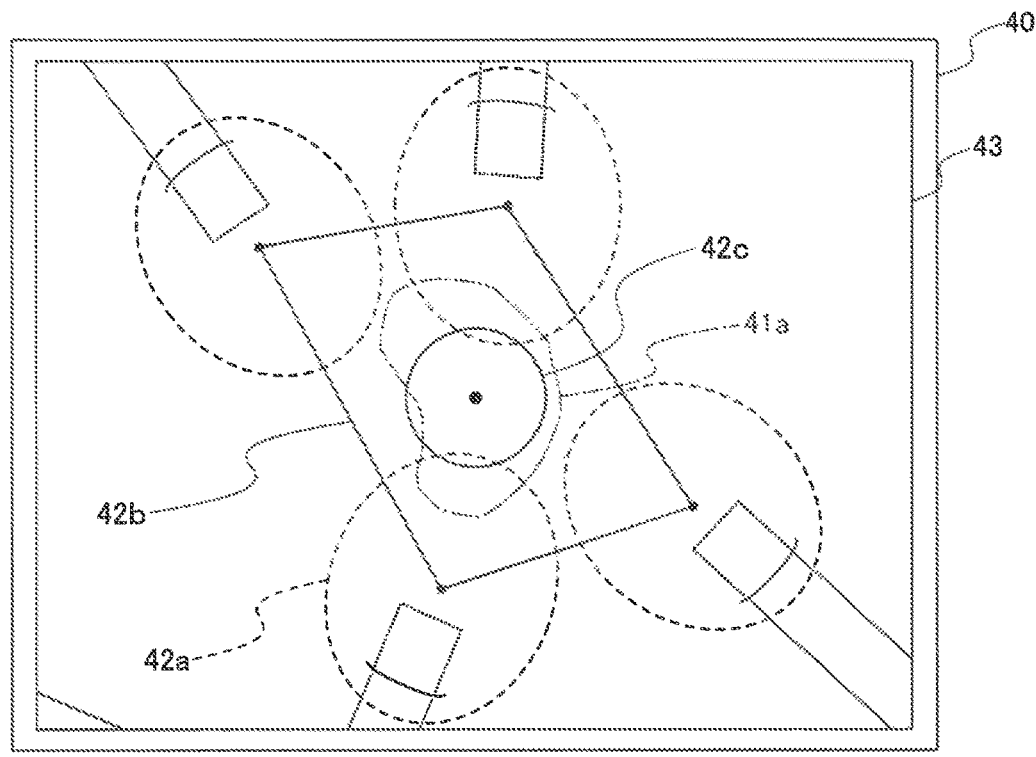
FIG. 7 is a diagram showing an example of a synthetic image displayed on a display unit.

Further, in the display unit 40, as shown in FIG. 7, a synthetic image 43 in which the fluorescent image 41 collected by the image collection unit 21 and the treatment light image 42 are superimposed may be displayed together with the first region of interest 42*c*. With this, a user, such as, e.g., a doctor, can simultaneously confirm the distribution 41*a* of the fluorescence, the treatment probes 52, and the positions of the treatment light, and the position of the first region of interest 42*c*. The treatment light regions 42*a* and the reference region 42*b* may not be displayed on the display unit 40, or may be switchable between display and non-display.

Figure 8:
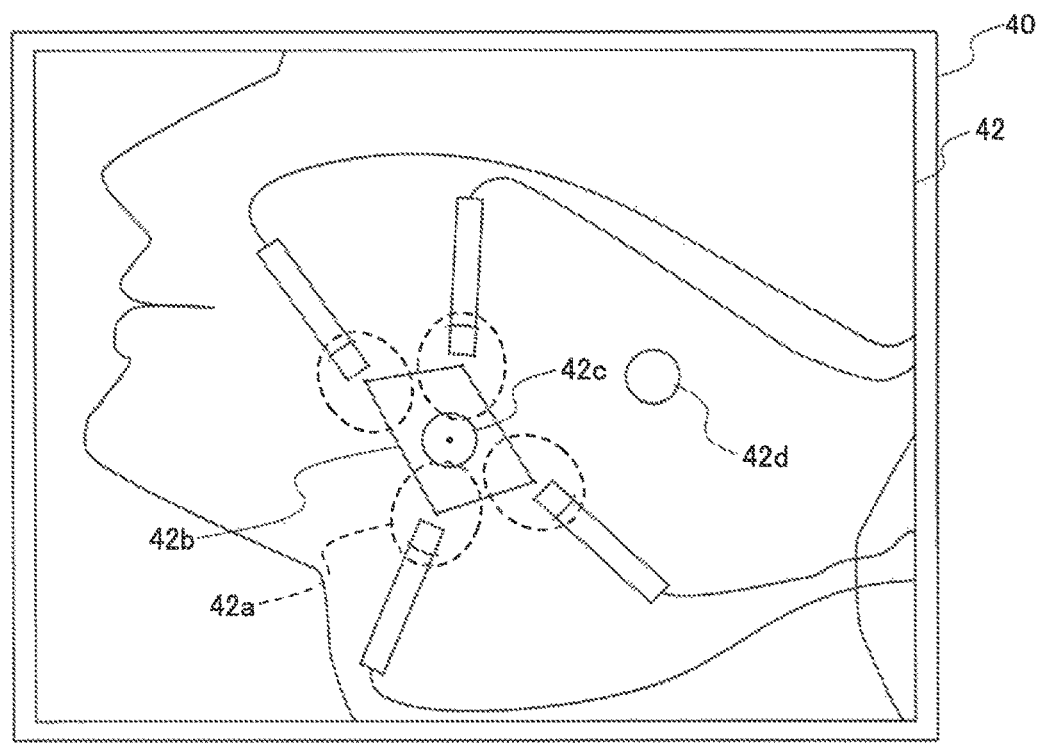
FIG. 8 is a diagram illustrating an example of a second region of interest set by a control unit of a treatment support device.

As shown in FIG. 8, the treatment support device 100 is configured to be able to set a second region of interest 42*d* at a position outside the positions of the treatment light in the treatment light image 42 captured by the treatment light imaging unit 14. The second region of interest 42*d* is a region for selectively acquiring the fluorescence intensity in the fluorescent image 41 for comparing with the fluorescence intensity in the fluorescent image 41 acquired in the first region of interest 42*c* set based on the position of the treatment light in the treatment light image 42. The control unit 23 is configured to perform control of limiting the setting of the region of the second region of interest 42*d* so as not to overlap the treatment light regions 42*a*, the region surrounded by the plurality of treatment light regions 42*a*, and the reference region 42*b* when the second region of interest 42*d* is set by a user, such as, e.g., a doctor.

That is, the second region of interest 42*d* is a region in which the treatment light is not emitted by the irradiation unit 50 and is a region in which no treatment is performed. Therefore, the fluorescence intensity in the second region of interest 42*d* is the fluorescence intensity of a region in which the fluorescent material of the medical agent 300 does not emit fluorescence and is fluorescence intensity serving as a reference index for completion of the treatment.

Figure 9:
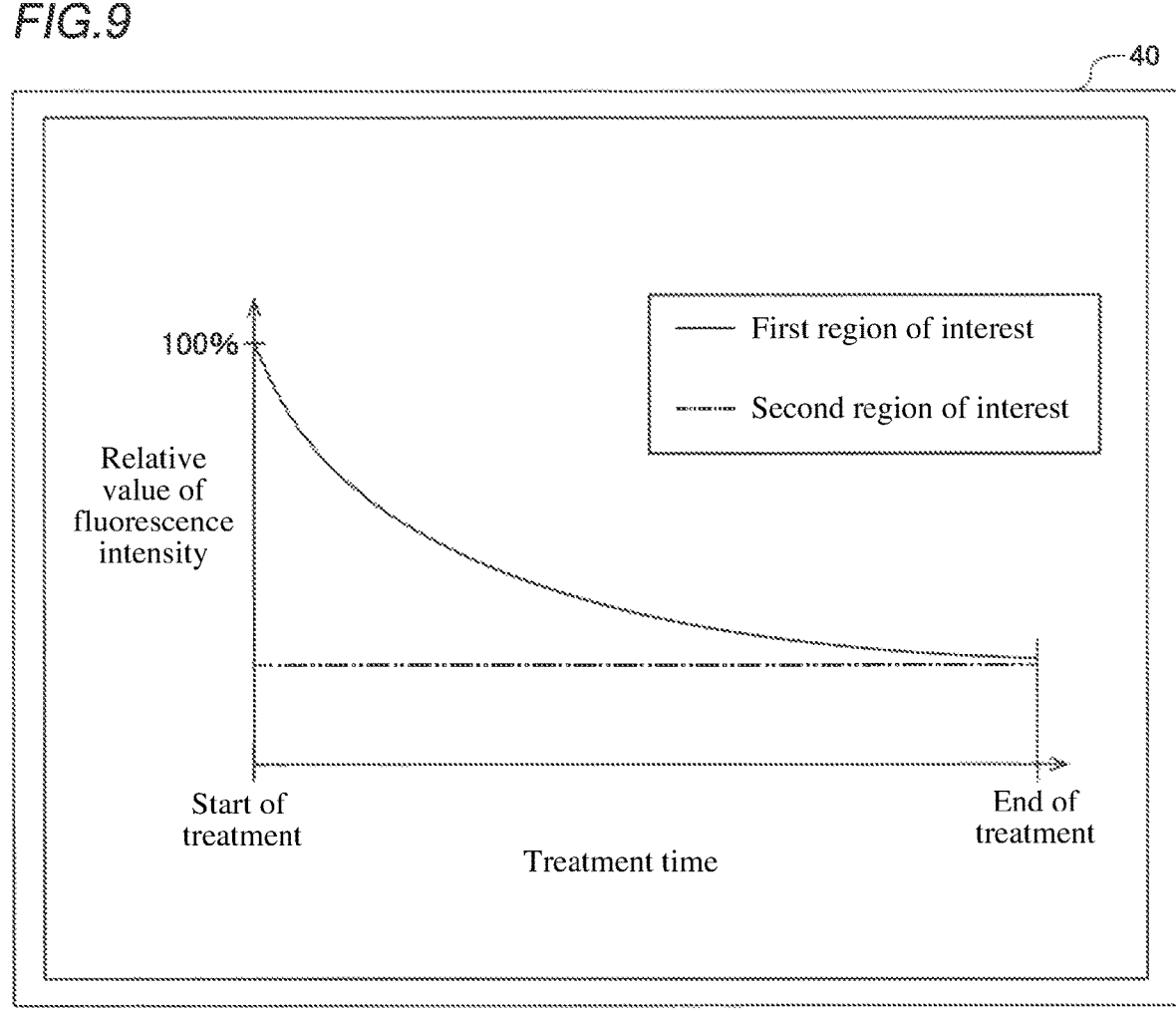
FIG. 9 is a diagram showing an example of a display by a display unit of a change in fluorescence intensity in a first region of interest and a change in fluorescence intensity in a second region of interest.

Further, the display unit 40 is configured to display the fluorescence intensity acquired in the first region of interest 42*c* and the fluorescence intensity acquired in the second region of interest 42*d* as shown in FIG. 9.

Specifically, in the display unit 40, the fluorescence intensity acquired in the first region of interest 42*c* and the fluorescence intensity acquired in the second region of interest 42*d* are displayed along the time series during the treatment. With this, the user, such as, e.g., a doctor, can compare the change in the fluorescence intensity in the first region of interest 42*c* with the fluorescence intensity in the first region of interest 42*c*. The fluorescence intensity displayed in the display unit 40 may not be a graph showing the change in the relative value of the fluorescence intensity during the treatment (see FIG. 9), and only the numerical value thereof may be displayed. Alternatively, the graph and the numerical value may be displayed simultaneously.

In the display unit 40, the treatment light image 42, the fluorescence intensity acquired in the first region of interest 42*c*, and the fluorescence intensity acquired in the second region of interest 42*d* may be displayed side by side at the same time. In addition, the display unit 40 may be configured to switch and display either one of the fluorescence intensity acquired in the fluorescent image 41, the treatment light image 42, the synthetic image 43, and the first region of interest 42*c*, and the fluorescence intensity acquired in the second region of interest 42*d*, or may be configured to display any one or all of them side by side at the same time. Alternatively, any one of them may be displayed in a superimposed manner.

Setting Processing of First Region of Interest

Figure 10:
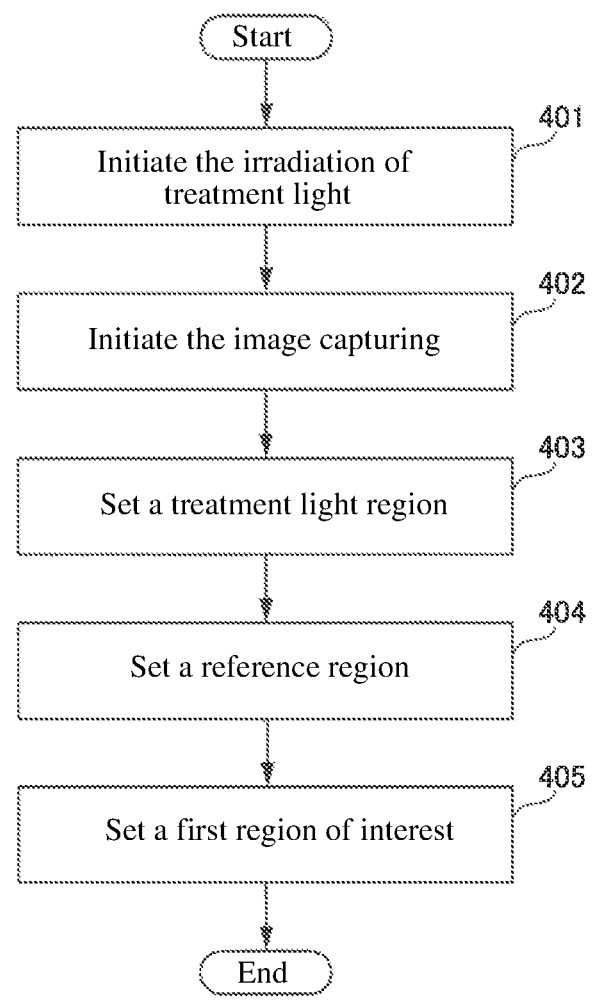
FIG. 10 is a flowchart illustrating an example of setting processing of a first region of interest performed by a control unit.

Next, referring to FIG. 10, the setting processing of the first region of interest 42*c* according to the control unit 23 of this embodiment will be described based on a flowchart.

In Step 401, the irradiation of the treatment light is initiated. In this embodiment, in the treatment of killing the cancer cell based on irradiating the medical agent 300 containing the fluorescent material administered into the body of the cancer patient 200 with the treatment light in a specific wavelength range, under the control of the control unit 23, the irradiation unit 50 irradiates the medical agent 300 administered into the body of the cancer patient 200 with the treatment light. The treatment light is emitted in the body of the cancer patient 200 by the treatment probe 52 inserted into the body of the cancer patient 200. Specifically, the treatment light is emitted in the body of the cancer patient 200 by the plurality of treatment probes 52 inserted into the body of the cancer patient 200 so as to surround the cancer to be subjected to the treatment.

In Step 402, image capturing is initiated. In this embodiment, the fluorescence imaging unit 13 initiates the image capturing of the fluorescent image 41 based on the fluorescence emitted by the fluorescent material of the medical agent 300 excited by the treatment light under the control of the control unit 23. That is, the fluorescence intensity of the fluorescence emitted by the fluorescent material of the medical agent 300 excited by the treatment light is acquired by the fluorescence imaging unit 13.

Further, the treatment light imaging unit 14 initiates imaging of the treatment light image 42 based on the treatment light under the control of the control unit 23. After initiating the imaging of the fluorescent image 41 by the fluorescence imaging unit 13 and the imaging of the treatment light image 42 by the treatment light imaging unit 14, the processing step moves to Step 403. Note that capturing of images, i.e., Step S402, may be initiated before or at the same time as the illumination of the treatment light (Step S401).

In Step 403, a plurality of treatment light regions 42*a* is set. In this embodiment, under the control of the control unit 23, the regions of the pixel in the treatment light image 42 in which the brightness of the light in the wavelength range of the treatment light is equal to or higher than a predetermined level is set as the plurality of treatment light regions 42*a* in the treatment light image 42. After setting the plurality of treatment light regions 42*a*, the processing step proceeds to Step 404.

In Step 404, the reference region 42*b* is set. In this embodiment, under the control of the control unit 23, the region surrounded by the geometric center positions of the plurality of treatment light regions 42*a* in the treatment light image 42 is set as the reference region 42*b*. After setting the reference region 42*b*, the processing step proceeds to Step 405.

In Step 405, the first region of interest 42*c* is set. In this embodiment, by the control of the control unit 23, the first region of interest 42*c*, which is a region for selectively acquiring the temporal change in the acquired fluorescence intensity, is set based on the positions of the treatment light in the captured treatment light image 42. The first region of interest 42*c* is set based on a plurality of treatment light regions 42*a* which are regions of the treatment light emitted from the plurality of treatment probes 52 in the captured treatment light image 42. After completing the setting of the first region of interest 42*c*, the control unit 23 ends the setting processing of the first region of interest 42*c*.

Effects of this Embodiment

In this embodiment, the following effects can be obtained.

In this embodiment, the treatment support device 100 is configured to be able to set the first region of interest 42*c*, which is a region for selectively acquiring the temporal change in the fluorescence intensity acquired by the fluorescence imaging unit 13, based on the positions of the treatment light in the treatment light image 42 captured by the treatment light imaging unit 14. With this, the treatment site at which the treatment to the cancer cell is performed can be easily specified based on the positions of the treatment light in the treatment light image 42. As a result, by associating the treatment light image 42 with the position of the fluorescence intensity acquired by the fluorescence imaging unit 13, it is possible to accurately set the first region of interest 42c, which is a region for selectively acquiring the temporal change in the fluorescence intensity acquired by the fluorescence imaging unit 13, in the region in which the progress of the treatment in the treatment site is desired to be grasped.

Further, the treatment light is excitation light for exciting the fluorescent material of the medical agent 300 and has energy larger than fluorescence. Therefore, it is easy to detect the treatment light as compared with fluorescence. This also makes it easier to specify the treatment site than when specifying the treatment site from the fluorescent image 41.

Further, in the treatment support device 100 according to the above-described embodiment, by having the following configuration, the following further effects can be obtained.

In addition, in this embodiment, the fluorescence imaging unit 13 is configured to acquire the fluorescent image 41 based on the fluorescence emitted by the fluorescent material of the medical agent 300 excited by the treatment light. With this, by associating the treatment light image 42 with the fluorescent image 41, it is possible to accurately set the first region of interest 42c which is a region for selectively acquiring the temporal change in the fluorescence intensity in the fluorescent image 41 more easily within the region in which the progress of the treatment in the treatment site is desired to be grasped. Further, the user can easily grasp the distribution state of the fluorescence emitted by the fluorescent material of the medical agent 300 by visually recognizing the fluorescent image 41.

Further, in this embodiment, the control unit 23 performs control for setting the first region of interest 42c based on the plurality of treatment light regions 42a which are regions of the treatment light emitted from the plurality of treatment probes 52 in the treatment light image 42 captured by the treatment light imaging unit 14. With this, the positions of the plurality of treatment light emitted from the plurality of treatment probes 52 are acquired by the treatment light image 42, and the treatment site can be specified based on the plurality of treatment light positions. Therefore, the first region of interest 42c can be more easily set in the treatment site.

In this embodiment, the treatment light image 42 is a color image captured based on the light in the wavelength range of the treatment light and the visible light. The control unit 23 sets a plurality of treatment light regions 42a in the treatment light image 42 based on the light in the wavelength range of the treatment light. As a result, the control unit 23 can easily set the plurality of treatment light regions 42a based on the color in the wavelength range of the treatment light from the treatment light image 42, which is a color image to be captured. Further, the user can easily specify the treatment site by visually recognizing the position of the treatment probe 52 and the color of the treatment light from the treatment light image 42, which is a color image to be imaged.

Further, in this embodiment, the control unit 23 sets the region of pixels in the treatment light image 42 in which the brightness of the light in the wavelength range of the treatment light is equal to or greater than a predetermined value as the plurality of treatment light regions 42a in the treatment light image 42. As a result, since region of pixels in the treatment light image 42 in which the brightness of the light in the wavelength range of the treatment light is equal to or greater than the predetermined value can be set as the plurality of treatment light regions 42a by the control unit 23, the plurality of treatment light regions 42a can be set more easily in the treatment light image 42.

Further, in this embodiment, the control unit 23 sets the first region of interest 42c based on each of the geometric center positions of the plurality of treatment light regions 42a in the treatment light image 42. With this, since the first region of interest 42c is set based on one point of each geometric center position of the treatment light region 42a, it is possible to suppress an increase in the processing load of the control unit 23 as compared with a case in which the first region of interest 42c is set based on all the pixels of the treatment light regions 42a which are regions of a plurality of pixels in the treatment light image 42 in which the brightness of the light in the wavelength range of the treatment light is equal to or greater than a predetermined value.

Further, in this embodiment, the control unit 23 sets the first region of interest 42c inside the reference region 42b, which is a region surrounded by the geometric center positions of the plurality of treatment light regions 42a in the treatment light image 42. With this, the inside of the region surrounded by the plurality of treatment probes 52 inserted in the body of the cancer patient 200 (subject) for emitting the treatment light can be set as the first region of interest 42c.

Further, in this embodiment, the control unit 23 sets the first region of interest 42c centering on the geometric center position of the reference region 42b to be smaller than the reference region 42b. With this, since the first region of interest 42c can be narrowed down to a small size by centering on the geometric center of the region surrounded by the plurality of treatment probes 52 for emitting the treatment light, it is possible to suppress an increase in the processing load of the control unit 23 as compared with the case in which the first region of interest 42c is larger than the reference region 42b.

In photoimmunotherapy, the destroyed cancer cell will become an antigen to immune cells. Therefore, a treatment effect can be expected in which the immune response of immune cells to the remaining cancer cell becomes effective. Thus, it is not always necessary to destroy all cancer cells in the treatment site by the treatment light, and adequate treatment can be performed by monitoring the progress of the treatment in the center part of the cancer cell.

Further, in this embodiment, the treatment support device 100 is configured to be able to set the second region of interest 42d, which is a region for selectively acquiring the fluorescence intensity in the fluorescent image 41 for comparing with the fluorescence intensity in the fluorescent image 41 acquired in the first region of interest 42c set based on the position of the treatment light image in the treatment light image 42, outward than the position of the treatment light in the treatment light image 42 captured by the treatment light imaging unit 14. With this, it is possible to set the second region of interest 42d to a region in which fluorescence is not emitted without being irradiated with the treatment light outside the position of the treatment light in the treatment light image 42 captured by the treatment light imaging unit 14. Consequently, by comparing the fluorescence intensity of the first region of interest 42c with that of the second region of interest 42d, the user can easily determine the degree of progress of the treatment.

In addition, in this embodiment, the display unit 40 displays the treatment light image 42, the fluorescence intensity acquired in the first region of interest 42c, and the fluorescence intensity acquired in the second region of the interest 42d. As a result, since the fluorescence intensity acquired in the first region of interest 42c and the fluorescence intensity acquired in the second region of interest 42d are displayed on the display unit 40, the user can easily compare the fluorescence intensity acquired in the first region of interest 42c with the fluorescence intensity acquired in the second region of interest 42d by the display of the display unit 40. As a result, the user can more easily determine the progress of the treatment by the display of the display unit 40.

In this embodiment, a method of setting a region of interest includes Step 405 for setting the first region of interest 42c, which is a region for selectively acquiring the temporal change in the acquired fluorescence intensity, based on the positions of the treatment light in the captured treatment light image 42. With this, the treatment site at which the treatment to the cancer cell is performed can be easily specified based on the positions of the treatment light in the treatment light image 42. As a result, by associating the treatment light image 42 with the position of the acquired fluorescence intensity, it is possible to accurately set the first region of interest 42c, which is a region for selectively acquiring the temporal change in the acquired fluorescence intensity, within a region in which it is desired to grasp the progress of the treatment at the treatment site.

Further, the treatment light is excitation light for exciting the fluorescent material of the medical agent 300 and has energy larger than the fluorescence, so that the treatment light can be easily detected as compared with the fluorescence. This also makes it easier to specify the treatment site than in the case of specifying the treatment site from the fluorescent image 41.

Further, in the method of setting the region of interest according to the above-described embodiment, the following further effects can be obtained by the following configuration.

Further, in this embodiment, Step 402 of acquiring the fluorescence intensity is a step of acquiring the fluorescent image 41 based on the fluorescence emitted by the fluorescent material of the medical agent 300 excited by the treatment light. Thus, by associating the treatment light image 42 with the fluorescent image 41, it is possible to accurately set the first region of interest 42c, which is a region for selectively acquiring the temporal change in the fluorescence intensity in the fluorescent image 41, more easily within the region in which the progress of the treatment at the treatment site is desired to be grasped. Further, the user can easily grasp the distribution state of the fluorescence emitted by the fluorescent material of the medical agent 300 by visually recognizing the fluorescent image 41.

Further, in this embodiment, according to the method of setting the region of interest, Step 405 of setting the first region of interest 42c based on the positions of the treatment light imaged by the treatment light imaging unit 14 is a step of setting the first region of interest 42c based on the plurality of treatment light regions 42a, which are regions of the treatment light emitted from the plurality of treatment probes 52 in the captured treatment light image 42. With this, it is possible to acquire the positions of the plurality of treatment light emitted from the plurality of treatment probes 52 by the treatment light image 42 and specify the treatment site based on the plurality of treatment light positions. Therefore, the first region of interest 42c can be more easily set in the treatment site.

Modifications

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, the above-described embodiment shows an example in which the first region of interest 42c is set by the control of the control unit 23, but the present invention is not limited thereto. In the present invention, the first region of interest may be set based on the positions of the treatment light in the treatment light image captured by the treatment light imaging unit by the manipulation of a user, such as, e.g., a doctor.

In addition, in the above-described embodiment, an example is shown in which the first region of interest 42c is set based on the plurality of treatment light regions 42a, which are regions of the treatment light emitted from the plurality of treatment probes 52 in the treatment light image 42 captured by the treatment light imaging unit 14, but the present invention is not limited thereto. In the present invention, the first region of interest may be set by the control of the control unit or the manipulation of th user, such as, e.g., a doctor, based on one treatment light region, which is a region of the treatment light emitted from one treatment probe in the treatment light image captured by the treatment light imaging unit.

Further, in the above-described embodiment, an example is shown in which the control unit 23 sets the treatment light region 42a in the treatment light image 42 based on the light in the wavelength range of the treatment light, but the present invention is not limited thereto. In the present invention, the control unit may set the treatment light region in the treatment light image based on the manipulation of the user, such as, e.g., a doctor.

Further, in the above-described embodiment, an example is shown in which the control unit 23 sets the first region of interest 42c based on each geometric center position of of the plurality of treatment light regions 42a in the treatment light image 42, but the present invention is not limited thereto. In the present invention, the control unit may set the first region of interest to include all of the plurality of treatment light regions in the treatment light image.

In addition, in the above-described embodiment, an example is shown in which the control unit 23 sets the first region of interest 42c inside the reference region 42b, which is a region surrounded by geometric center positions of the plurality of treatment light regions 42a in the treatment light image 42, but the present invention is not limited thereto. In the present invention, the control unit may be set the reference region as the first region of interest, or may set a part of the first region of interest outside the reference region.

In the above-described embodiment, an example is shown in which the control unit 23 sets the first region of interest 42c to be smaller than the reference region 42b centering on the geometric center position of the reference region 42b, but the present invention is not limited thereto. In the present invention, the control unit may set the first region of interest, i.e., the position and the size, by the manipulation of the user, such as, e.g., a doctor, inside the reference region.

In the above-described embodiment, an example is shown in which the control unit 23 sets the circular first region of interest 42c centering on the geometric center position of the reference region 42b inside the reference region 42b, but the present invention is not limited thereto. In the present invention, the control unit may set the first region of interest as an arc shape, a rectangular shape, or a shape depicted by a freely curved shape. Further, in the same manner, the second region of interest may be set as an arc shape, a rectangular shape, or a shape depicted by a freely curved shape.

Further, in the above-described embodiment, an example is shown in which the second region of interest 42d is configured to be able to be set outward than the position of the treatment light in the treatment light image 42 captured by the treatment light imaging unit 14, but the present invention is not limited thereto. In the present invention, the second region of interest may be set in the fluorescent image by the control of the control unit or the manipulation by a user, such as, e.g., a doctor.

Further, in the above-described embodiment, an example is shown in which the display unit 40 shows the treatment light image 42, the fluorescence intensity acquired in the first region of interest 42c, and the fluorescence intensity acquired in the second region of interest 42d are displayed, but the present invention is not limited thereto. In the present invention, instead of the fluorescence intensity acquired in the second region of interest, the display unit may display a fluorescence intensity which becomes an indicator of completion of the treatment stored in advance in the device.

Further, in the above-described embodiment, an example is shown in which the control unit 23 built-in the device main body 20 of the treatment support device 100 is configured to analyze the fluorescent image 41 and the treatment light image 42 and analyze the information on the fluorescence intensity of the fluorescent image 41 for each time series, but the present invention is not limited thereto.

Figure 11:
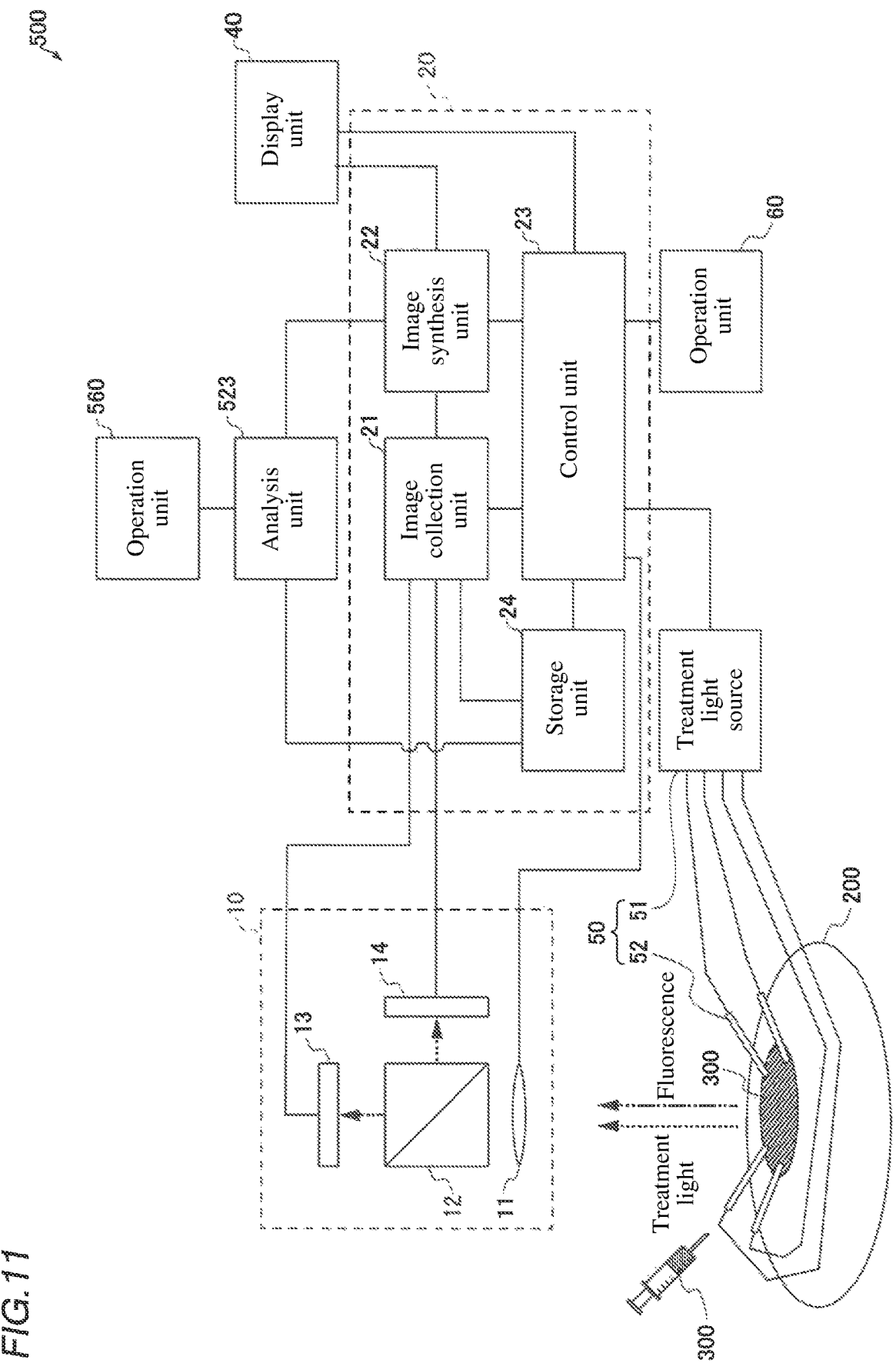
FIG. 11 is a block diagram showing a configuration of a treatment support device according to a first modification of one embodiment of the present invention.

In the present invention, as in the treatment support device 500 according to the first modification shown in FIG. 11, an analysis unit 523 for analyzing the fluorescent image 41 and the treatment light image 42 and analyzing the information on the fluorescence intensity for each time series in the fluorescent image 41 may be provided outside the device main body 20. The analysis unit 523 is configured to be capable of performing data communication with the image synthesis unit 22 and the storage unit 24 built-in the device main body 20, and performs an analysis based on the data of the image synthesized by the image synthesis unit 22 and the data of the image stored in the storage unit 24. Further, in the treatment support device 500 according to the first modification, the operation unit 560 for accepting operations for the analysis of the analysis unit 523 by a user, such as, e.g., a doctor, is provided outside the device main body 20. The analysis unit 523 is, for example, a PC (Personal Computer), and the operation unit 560 includes, for example, a touch panel, a keyboard, a mouse, or the like.

In addition, in the above-described embodiment, an example is shown in which the treatment light imaging unit 14 captures an image based on the visible light including the treatment light, but the present invention is not limited thereto. In the present invention, the imaging unit of the treatment support device may be provided with a treatment light imaging unit for capturing the treatment light image based on the treatment light and a visible light imaging unit for capturing the visible light image based on the visible light, separately.

Further, in the above-described embodiment, for convenience of explanation, although the setting processing of the first region of interest 42c of the present invention is described using a flow-driven flowchart in which processing is performed in order along the processing flow, but the present invention is not limited thereto. In the present invention, the processing operation may be performed by event-driven type processing that executes processing on an event-by-event basis. In this case, the processing operation may be performed in a complete event-driven fashion or in combination of event-driven type processing and flow-driven type processing.

Further, in the above-described embodiment, an example is shown in which the first region of interest 42c is set by associating the treatment light image 42 with the fluorescent image 41, but the present invention is not limited thereto. In the present invention, the first region of interest may be set by associating the treatment light image with the electric signals photoelectrically converted by imaging elements from the fluorescence emitted by the fluorescent material of the medical agent.

(Aspects)

It will be understood by those skilled in the art that the above-described exemplary embodiments are concrete examples of the following aspects.

Item 1

A treatment support device comprising:
an irradiation unit configured to emit treatment light in a specific wavelength range to a medical agent administered to a body of a subject when performing treatment for killing a cancer cell, the medical agent containing a fluorescent material;
a fluorescence intensity acquisition unit configured to acquire fluorescence intensity of fluorescence emitted by the fluorescent material of the medical agent excited by the treatment light; and
a treatment light imaging unit configured to capture a treatment light image based on the treatment light,
wherein the treatment support device is configured such that a first region of interest is capable of being set based on a position of the treatment light in the treatment light image captured by the treatment light imaging unit, the first region of interest being a region for selectively acquiring a temporal change in the fluorescence intensity acquired by the fluorescence intensity acquisition unit.

Item 2

The treatment support device as recited in the above-described Item 1, wherein the fluorescence intensity acquisition unit is configured to acquire a fluorescent image based on the fluorescence emitted by the fluorescent material of the medical agent excited by the treatment light.

Item 3

The treatment support device as recited in the above-described Item 2,
wherein the irradiation unit includes a treatment probe configured to be inserted into the body of the subject to emit the treatment light in the body of the subject,
wherein a plurality of the treatment probes is provided, and
wherein the treatment support device further comprises a control unit configured to control to set the first region of interest based on a plurality of treatment light regions, each of the treatment light regions being a region of the treatment light emitted from each of the plurality of treatment probes in the treatment light image captured by the treatment light imaging unit.

Item 4

The treatment support device as recited in the above-described Item 3,
wherein the treatment light image is a color image captured based on the treatment light and light in a wavelength range of visible light, and wherein the control unit is configured to set the plurality of treatment light regions in the treatment light image based on light in a wavelength range of the treatment light.

Item 5

The treatment support device as recited in the above-described Item 4,
wherein the control unit is configured to set regions of pixels in the treatment light image in which brightness of the light in the wavelength range of the treatment light is equal to or greater than a predetermined value as the plurality of treatment light regions in the treatment light image.

Item 6

The treatment support device as recited in any one of the above-described Items 3 to 5,
wherein the control unit is configured to set the first region of interest based on each of geometric center positions of the plurality of treatment light regions in the treatment light image.

Item 7

The treatment support device as recited in any one of the above-described Item 3 to 6,
wherein the control unit is configured to set the first region of interest inside a reference region which is a region surrounded by geometric center position s of the plurality of treatment light regions in the treatment light image.

Item 8

The treatment support device as recited in the above-described Item 7,
wherein the control unit is configured to set the first region of interest so as to be smaller than the reference region, centering on a geometric center position of the reference region.

Item 9

The treatment support device as recited in any one of the above-described Items 3 to 8,
wherein a second region of interest is configured to be capable of being set outside the position of the treatment light in the treatment light image captured by the treatment light imaging unit, the second region of interest being a region for selectively acquiring the fluorescence intensity in the fluorescent image acquired in the first region of interest in order to compare with the fluorescence intensity in the fluorescent image acquired in the first region of interest set based on the position of the treatment light in the treatment light image.

Item 10

The treatment support device as recited in the above-described Item 9, further comprising
a display unit configured to display the treatment light image, the fluorescence intensity acquired in the first region of interest, and fluorescence intensity acquired in the second region of interest.

Item 11

A method of setting a region of interest, comprising the steps of:
emitting treatment light in a specific wavelength range to a medical agent administered to a body of a subject when performing treatment for killing a cancer cell, the medical agent containing a fluorescent material;
acquiring fluorescence intensity of fluorescence emitted by the fluorescent material of the medical agent excited by the treatment light;
capturing a treatment light image based on the treatment light; and
setting a first region of interest based on a position of the treatment light in the treatment light image captured, the first region of interest being a region for selectively acquiring a temporal change in the fluorescence intensity acquired.

Item 12

The method of setting a region of interest as recited in the above-described Item 11,
wherein the step of acquiring the fluorescence intensity is a step for acquiring a fluorescent image based on the fluorescence emitted by the fluorescent material of the medical agent excited by the treatment light.

Item 13

The method of setting a region of interest as recited in the above-described Item 12,
wherein the step of emitting the treatment light is a step of emitting the treatment light in the body of the subject by a plurality of treatment probes inserted into the body of the subject, and
wherein the step of setting the first region of interest based on the position of the treatment light in the treatment light image in which the first region of interest is imaged is a step of setting the first region of interest based on a plurality of treatment light regions that are regions of treatment light emitted from each of the plurality of treatment probes in the treatment light image captured.

The invention claimed is:

1. A treatment support device comprising:
a fluorescence intensity acquirer configured to acquire fluorescence intensity of fluorescence emitted by fluorescent material of a medical agent excited by treatment light from an irradiator including a plurality of treatment probes which are configured to be inserted into a body of a subject from outside the body of the subject and irradiate the treatment light inside the body of the subject;
a treatment light imager configured to capture a treatment light image based on the treatment light; and
a controller,
wherein the controller is configured to:
set a plurality of treatment light regions corresponding to each of said plurality of treatment probes based on the treatment light image,
calculate position information for each of the plurality of treatment light regions,
set a reference region based on the position information for each of the plurality of treatment light regions, and
set a first region of interest, which is a region in which the fluorescence intensity acquirer acquires a time variation of the fluorescence intensity, so that a portion of the first region of interest is included inside the reference region.

2. The treatment support device as recited in claim 1,
wherein the fluorescence intensity acquirer is configured to acquire a fluorescent image based on the fluorescence emitted by the fluorescent material of the medical agent excited by the treatment light.

3. The treatment support device as recited in claim 2,
wherein the treatment light image is a color image captured based on the treatment light and light in a wavelength range of visible light, and wherein the controller is configured to set the plurality of treatment light regions in the treatment light image based on light in a wavelength range of the treatment light.

4. The treatment support device as recited in claim 3, wherein the controller is configured to set regions of pixels in the treatment light image in which brightness of the light in the wavelength range of the treatment light is equal to or greater than a predetermined value as the plurality of treatment light regions in the treatment light image.

5. The treatment support device as recited in claim 2, wherein the controller is configured to set the first region of interest based on each of geometric center positions of the plurality of treatment light regions in the treatment light image.

6. The treatment support device as recited in claim 2, wherein the controller is configured to set the first region of interest inside reference region which is a region surrounded by geometric center positions of the plurality of treatment light regions in the treatment light image.

7. The treatment support device as recited in claim 6, wherein the controller is configured to set the first region of interest so as to be smaller than the reference region centering on a geometric center position of the reference region.

8. The treatment support device as recited in claim 2, wherein the controller is further configured to set a second region of interest outside the position of the treatment light in the treatment light image captured by the treatment light imager, the second region of interest being a region for selectively acquiring the fluorescence intensity in the fluorescent image acquired in the first region of interest in order to compare with the fluorescence intensity in the fluorescent image acquired in the first region of interest set based on the position of the treatment light in the treatment light image.

9. The treatment support device as recited in claim 8, further comprising:

a display configured to display the treatment light image, the fluorescence intensity acquired in the first region of interest, and fluorescence intensity acquired in the second region of interest.

10. A method of setting a region of interest, comprising the steps of:

emitting treatment light in a specific wavelength range to a medical agent administered to a body of a subject from a plurality of treatment probes which are inserted into the body from outside the body of the subject and irradiate the treatment light inside the body of the subject, when performing treatment for killing a cancer cell, the medical agent containing a fluorescent material;

acquiring fluorescence intensity of fluorescence emitted by the fluorescent material of the medical agent excited by the treatment light;

capturing a treatment light image based on the treatment light;

setting a plurality of treatment light regions corresponding to each of said plurality of treatment probes based on the treatment light image;

calculating position information for each of the plurality of treatment light regions;

setting a reference region based on the position information for each of the plurality of treatment light regions; and setting a first region of interest, which is a region in which a time variation of the fluorescence intensity is acquired, so that a portion of the first region of interest is included inside the reference region.

11. The method of setting a region of interest as recited in claim 10, wherein the step of acquiring the fluorescence intensity comprises acquiring a fluorescent image based on the fluorescence emitted by the fluorescent material of the medical agent excited by the treatment light.

* * * * *